United States Patent [19]

Sun et al.

[11] 4,323,457

[45] Apr. 6, 1982

[54] ARTIFICIAL ENDOCRINE PANCREAS

[75] Inventors: Anthony M. Sun; Wolf J. Parisius, both of Willowdale, Canada

[73] Assignee: Connaught Laboratories Limited, Willowdale, Canada

[21] Appl. No.: 781,001

[22] Filed: Mar. 24, 1977

[30] Foreign Application Priority Data

Mar. 21, 1977 [CA] Canada .................................. 274354

[51] Int. Cl.³ ...................... B01D 31/00; B01D 13/00
[52] U.S. Cl. .................................. 210/645; 210/321.1
[58] Field of Search .................... 210/22, 321 B, 497.1

[56] References Cited

U.S. PATENT DOCUMENTS

| 3,228,876 | 1/1966 | Mahon | 210/22 |
| 3,396,849 | 8/1968 | Lande et al. | 210/321 B |
| 3,734,851 | 5/1973 | Matsumura | 210/22 |
| 3,794,468 | 2/1974 | Leonard | 210/497.1 X |
| 3,827,565 | 8/1974 | Matsumura | 210/22 |
| 3,902,490 | 9/1975 | Jacobsen et al. | 210/321 B X |

OTHER PUBLICATIONS

Nose et al., "An Experimental Artificial Liver Utilizing Extracorporeal Metabolism with Sliced or Granulated Canine Liver" from Trans. Amer. Soc. Artif. Int. Organs, vol. IX, 1963, pp. 358–362.

Primary Examiner—Frank A. Spear, Jr.
Attorney, Agent, or Firm—Cushman, Darby & Cushman

[57] ABSTRACT

The artificial endocrine pancreas device comprises a container in which are provided one, or more, hollow fibres; in the container and on the outside of the fibres are placed pancreatic islet cells; each fibre has a porosity allowing substances of molecular weight less than 100,000 Daltons to pass through so that blood passing in the hollow fibres can pass nutrients to the cells and pick up hormones, but no antigen or antibody with a molecular weight above 100,000 Daltons can pass through.

12 Claims, 3 Drawing Figures

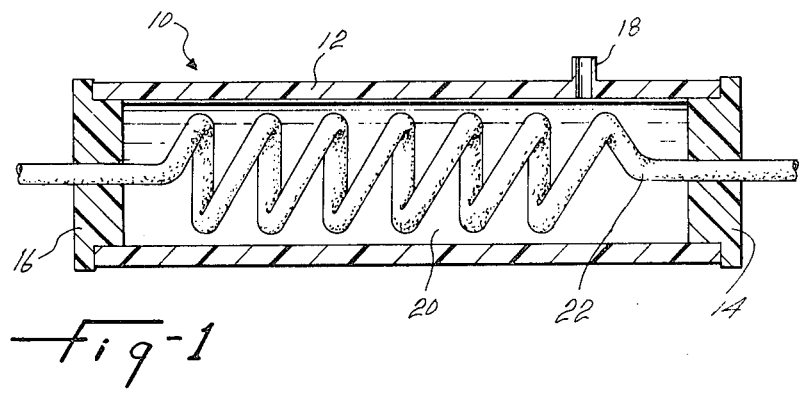
_fig-1_
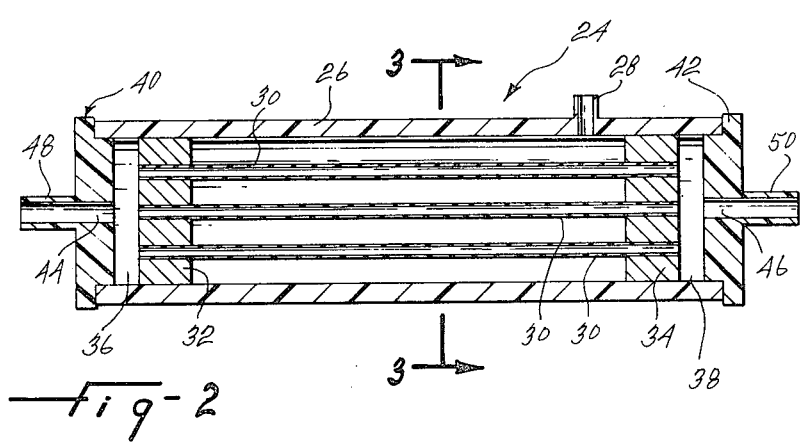
_fig-2_
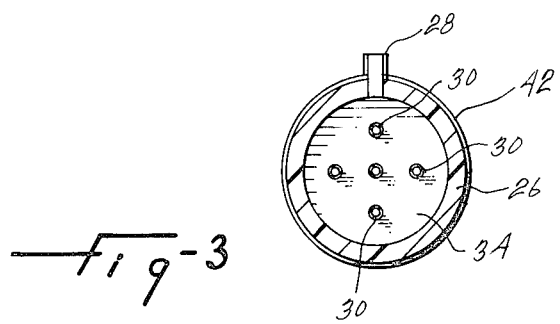
_fig-3_

ARTIFICIAL ENDOCRINE PANCREAS

FIELD OF THE INVENTION

This invention relates to a device for use as an artificial endocrine pancreas and to a method for treating blood or other body fluid by means of a device through which blood flows, and the hormone, insulin, is released on physiological demand from the device into the blood in order to maintain normal levels of circulating blood glucose.

BACKGROUND OF THE INVENTION

In spite of the general use of insulin, since its discovery more than 50 years ago, diabetes and its associated problems are still a major concern in world health. It is recognized that insulin, when injected, is only a treatment for certain facets of the disease and not a cure. Whilst millions of diabetics have been able to live normal lives, with greatly increased life spans, there are still complications of the disease, such as renal, cerebral and cardiovascular problems that are not controlled by the daily injection of the hormone. The intermittent administration of insulin and its release on a continuing basis, from Lente type materials, rather than the on-off response to physiological demand, such as is experienced with competent Islets of Langerhans, are thought to be responsible for the failure of insulin to control the complications of the disease. This seems to be especially true of the early onset diabetic, where the islets play unknown roles in the metabolism of vascular and neural tissues. In addition, it is known that 5 to 10% of diabetics develop resistance to the injected insulin and require ever increasing doses to maintain a controlled status.

Since the advent of transplantation surgery and its associated techniques, it would seem that diabetes might be cured, rather than treated, by the transplantation of pancreatic tissue from a donor. As with any transplantation technique, the surgeon is faced with rejection problems and accurate blood typing is required. It is apparent from information accumulated over the years, that different organs have different degrees of rejection associated with them. Drugs are needed, in any organ transplant, to suppress the antibodies formed by the host to the foreign implanted tissue, but also suppress immunity to common diseases and infections. From the limited data available, it is apparent that even with maximum care, transplantation of the pancreas is subject to even greater rejection problems than heart transplants. Data indicate that there has been no successful pancreatic transplant to date, maximum survival times being less than a year.

Attempts have been made to devise artificial pancreas which by monitoring glucose levels continuously and releasing insulin on demand keep the diabetic controlled in several aspects. One method requires the use of fast analytical techniques to determine the glucose level. This analysis has to be automatic and the results transferable to a mechanical means of adding insulin to the circulatory system to keep glucose levels within normal limits. Such a method is being used for those diabetics who are called "brittle", that is their daily insulin requirements are such that the balance between too high a glucose level and too high an insulin level is very difficult to maintain with an ordinary injection regime. Because of the associated assay equipment, the type of device used to carry out this method is large and the patient involved is permanently bedridden beside the apparatus. Even with present day miniaturization, it seems unlikely that such an instrument can be readily reduced to a portable machine.

A logical extension of the above techniques would be an artificial pancreas utilizing living tissue, that would not involve rejection phenomena, and would supply insulin to the patient depending on the circulating blood sugar levels as determined by biochemical reactions, rather than by mechanical means. One artificial endocrine pancreas is described in U.S. Pat. No. 3,827,565 issued Aug. 6, 1974 to Kenneth N. Matsumura and includes a flat membrane positioned in contact on one side thereof with the body fluid to be treated and on the opposite side thereof with live pancreatic islet cells. In addition to doubts whether the device has ever been used clinically, there is the further doubt of its operation since it is well known that if blood flows over a flat surface it is proned to coagulation.

OBJECT OF THE INVENTION

It is an object of the present invention to overcome the problem of immune rejection of transplanted tissue by providing a capillary unit in which competent islets are separated from circulating blood by a barrier which permits cross-over of low molecular weight substances, such as glucose and insulin, but not of high molecular weight components such as antibodies and antigens.

It is known that mammalian cells can be kept viable in vitro using a variety of conditions and suitable tissue culture media. Thus in the production of viral vaccines, where living cell cultures are infected with virus and the propagated virus harvested and used for vaccine production, several types of cells from a variety of species have been grown successfully. Examples of these are monkey kidney, duck embryo, etc. More recently, continuous cell lines which retain normal diploid characteristics have been developed, such as human diploid cells, notably those defined as WI-38 and MRC-5. To this end, methods have been used that involve the use of specific culture media such as CMRL-1969 ®.

The techniques developed for these types of in vitro cell cultures are applied to the production, in vitro, of viable islets of Langerhans, which are the hormone productive entities within the pancreas of mammalian species. It has been observed that under the conditions of culture used, the islets continue to produce insulin. It can also be seen under a microscope that after some days of culture, the original islets rupture and some of the constituent β-cells are multiplying outside the islet. The β-cells are the actual producers of insulin and it will be understood that when the expressions "islet cells" or "islets" are used, these cover the constituent cell types within the islet of Langerhans, including β-cells.

To avoid rejection problems and the use of immunosuppressive drugs, the production of antibodies to the foreign tissue must not occur and should some antibodies form, they must not be able to approach the islets. The fibre used with the present invention has pores that are of such a size that molecules of certain dimensions cannot pass through. Because size can be related to molecular weight, the porosity of the fibre used is said to allow diffusion of substances excluding those with molecular weights over a certain figure. It must be pointed out that this is not a precise figure and a fibre that is quoted as having a pore size excluding molecules with a molecular weight, say of 100,000 Daltons, means that no molecule having a molecular weight over this size could pass through the pores, but also many molecules of say 85,000 or 95,000 Daltons could be wholly or partially excluded. Using a fibre or membrane having an exclusion of 100,000 Daltons would mean that neither antigens nor antibodies could pass through the pores, since most antigens are cell surface associated and bound and antibodies are known to have molecular weights of at least 150,000 Daltons. Thus, cells on one side of such a membrane or fibre would not be affected by, or destroyed by, an antibody on the other side.

The present invention therefore relates to a device for use as an artificial pancreas and comprises: container means for receiving pancreatic islet cells therein; and one or more hollow fibres disposed in the container means, each fibre having a porosity allowing materials of molecular weight less than 100,000 Daltons to pass through.

In one preferred form of the invention, there is only one fibre in the container, which fibre is coiled in shape to obtain increased surface area with the islet cells.

The scope of applicability of the present invention will become apparent from the detailed description given hereinafter; it should be understood, however, that this description while indicating preferred embodiments of the invention is given by way of illustration only since various changes and modifications within the spirit and scope of the invention will become apparent to those skilled in the art from reading the following description.

IN THE DRAWINGS

FIG. 1 is an elevation cross-sectional view of a first embodiment of an artificial pancreas device made in accordance with the present invention;

FIG. 2 is an elevation cross-sectional view of another embodiment thereof;

FIG. 3 is a transverse cross-sectional view taken along lines 3-3 of FIG. 2.

DESCRIPTION OF PREFERRED EMBODIMENTS

Referring to FIG. 1, the artificial pancreas device 10 consists of a cylindrically shaped container 12 which is sealingly closed at opposite ends by means of end plates 14 and 16 to form an enclosed chamber 20. An inlet port 18 is provided to allow insertion of pancreatic islet cells (not shown) inside chamber 20. Extending through the container is a single hollow fibre 22, the walls of which have a pore size which excludes molecules of molecular weight greater than 100,000 Daltons. The fibre may be a polyvinyl chloride acrylic copolymer, such as the one manufactured by the Amicon Corporation and designated P-100; such fibre has an internal diameter of 500 $\mu$m.

In the embodiment of the invention illustrated in FIG. 1, the portion of the fibre inside chamber 20 is coiled to provide increased surface area with the pancreatic islet cells when inserted in the chamber. The opposite ends of the fibre extend through end plates 14 and 16 and outside the container for connection to a supply of body fluid to be treated. Coil fibre 22 could be further coiled to provide further additional surface area.

Referring to FIGS. 2 and 3, there is shown another embodiment of a pancreas device 24 made in accordance with the present invention; device 24 consists of a cylindrically shaped body 26 having an inlet port 28 for the insertion of the pancreatic islet cells therein and of a bundle of spaced distributed hollow fibres 30, the fibres being received at their opposite ends 32 and 34 to a mass of sealant material, such as epoxy resin. The fibre extremities terminate in end chambers 36 and 38 defined by plates 40 and 42, respectively, which are mounted flat against the end of container 26. An opening 44, 46 is provided in each plate so that the device may be connected to a source of fluid to be treated by fine tubings 48 and 50, preferably made of Teflon (trademark); however, this material may be made of any other material which is compatible with biological fluids.

The container may be made of a number of materials but a clear plastic material, such as plexiglass (trademark), should preferably be used. Fibres 30 have a pore size which excludes substances of molecular weight greater than 100,000 Daltons.

The use of the device as an artificial pancreas will now be described. Inside containers 12, 26 and outside fibres 22, 30 is placed a medium to support the growth of cells. It may be one of a number of media well known to those skilled in the art; one example, is the medium known under the trademark CMRL-1969. Into this medium inside the container, islet cells are placed which have been isolated from an animal using techniques which are known to those skilled in the art. The transfer of the cells and media is achieved using aseptic techniques. Medium is then perfused through the fibres employing sterile medium and a peristaltic pump to circulate it. The medium is changed at stated intervals and the physiological competence of the cells is determined by the concentration of insulin in the circulating fluid. Using such system, it has been determined that islets can remain alive and functional for at least six months. If, after a relatively short time on this in vitro system, the islets are still viable and the circulating medium contains no adventitious agents, the device can then be connected to an animal in such a way that the animal's blood flows through the fibres continuously. Because the present invention employs a fibre that excludes molecules with molecular weights greater than 100,000 Daltons, the cells within the container are not subject to rejection phenomena because neither antigens nor antibodies can pass through the fibre. In addition, this means that accurate typing of the donor cells is not necessary. In fact, it has been found that donor cells of one species can control the diabetic syndrome of an animal from a completely different species; as an example, it has been found that pancreatic cells from a rat may be used with the present device to control the diabetic state of a monkey.

Because the number of islets required in the present device is relatively small and, as they can be kept viable in a small amount of medium, a device containing sufficient islets or cells that could convert a diabetic animal, such as a monkey or man, to normal, could be made small enough so that it may be used to be implanted under the skin. Therefore, the device of the present invention is further characterized in that it is portable and would allow a recipient to return to normal life without being tied to an unwieldy piece of apparatus.

The following examples are provided as illustrative of the present invention. The enumeration of detail, however, is not to be considered as restrictive of the scope of the invention.

EXAMPLE 1

Islets were isolated from rat pancreata using a modification of the method of Lacy and Kostianovsky and purified by Ficoll gradient centrifugation. Briefly, chopped pancreas was incubated with collagenase at 37° C. and most of the digested acinar tissue removed with a syringe under a dissection microscope. The remaining tissue as mixed with 25% Ficoll solution in a centrifuge tube and two Ficoll concentrations (16%, 11%) layered above the suspension. Centrifugation was carried out at 500 g for 20 to 25 minutes and the islets harvested from the interface of the 25% and 15% Ficoll layers. Approximately 1,000 to 1,500 islets, so collected, were injected into the device using aseptic techniques. The device was perfused with medium CMRL-1969 supplemented with 7.5% foetal calf serum and antibiotics for two to three days and the insulin content of the circulating medium monitored using a radioimmunoassay.

Wistar rats weighing 150 g to 200 g, and rendered diabetic using injections of streptozotocin, were anaesthetized with ether and dissected to reveal the carotid artery and jugular vein. The device, containing islet cells, was connected between these two vessels using canulation, with a T-connection being inserted between the artery and the unit to allow for the constant addition of heparin solution, to avoid blood coagulation. In addition, a control group of diabetic animals was set up in a similar fashion, but where no islets were placed in the device. A final group of normal rats were also attached to the device, without islets in the container. The results are shown in Table 1. As can be seen the blood glucose of diabetic rats with the present device, containing islets, attached was lowered from an average of 420 mg % to 132 mg % within one hour of attachment, and remained at this level for the duration of the experiment. Blood sugars in the control groups remained constant, showing no shock effects from the attachment of the device.

TABLE 1

Blood Glucose Levels (mg %) in Normal and Diabetic Rats with "Artificial Pancreas" Attached

| Hours | 0 | 1 | 4 | 10 | 18 | 24 | 48 |
|---|---|---|---|---|---|---|---|
| Diabetic Rats (A) (Artificial Pancreas Device with Islets) | 420 | 132 | 120 | 152 | 266 | 182 | 141 |
| Diabetic Rats (B) | 455 | 418 | 386 | 428 | 302 | 389 | 292 |
| Normal Rats (C) | 138 | 152 | — | — | — | 147 | 118 |

In Groups B and C the animals were connected to artificial pancreata without islets.

EXAMPLE 2

Islets were isolated from rat pancreata as detailed in the previous example. The collected cells—in this case some 6000—were put into the pancreas device using aseptic techniques. A Cyhomolgus monkey, rendered diabetic by partial pancreatectomy and treatment with streptozotocin, was operated on and the femoral artery and femoral vein exposed. The device was attached by canulation and a T-junction for the addition of heparin solution was placed between the artery and the device. The monkey was restrained and blood glucose monitored. The results are shown in Table 2. As can be seen the blood glucose was considerably lowered from starting levels.

TABLE 2

Blood Glucose Levels (mg %) in a Diabetic Monkey with "Artificial Pancreas" Attached

| Hours | 0 | .25 | .5 | 1 | 2 | 4 | 8 | 18 | 21.5 |
|---|---|---|---|---|---|---|---|---|---|
| Blood Glucose mg % | 220 | 195 | 175 | 157 | 135 | 90 | 127 | 285 | >400 |

What is claimed is:

1. A device for use as an artificial pancreas comprising: container means for receiving pancreatic islet cells therein; one or more hollow fibres in said container means, each said fibre having a porosity allowing only substances of molecular weight less than 100,000 Daltons to pass through.

2. A device as defined in claim 1, comprising a single fibre in a coiled shape to obtain increased surface area.

3. A device as defined in claim 1, comprising a bundle of said fibres in spaced evenly distributed arrangement in said container means.

4. A device as defined in claim 1, wherein said container means include inlet means for placing pancreatic islet cells therein and means for connecting the opposite end portions of said one or more fibres to a supply of body fluid to be treated.

5. An artificial endocrine pancreas device comprising: a container defining an enclosed chamber; one or more hollow fibres extending from opposite ends of said container and having the opposite end portions thereof in attachment with a supply of body fluid to be treated; pancreatic islet cells in said chamber in proximity of the outside wall of said one or more fibres; said one or more fibres each having a porosity allowing substances, in said body fluid, of molecular weight less than 100,000 Daltons to diffuse in said chamber to thereby treat said body fluid.

6. An artificial endocrine pancreas device as defined in claim 5, which, when attached to an animal, has pancreatic inlet cells of the same species as that of said animal.

7. An artificial endocrine pancreas device as defined in claim 5, which, when attached to an animal, has pancreatic islet cells of a different species than that of said animal.

8. An artificial endocrine pancreas device as defined in claim 5, comprising a single fibre in a coiled shape to thereby obtain increased surface area.

9. A process for treating a body fluid comprising: placing in a container defining an enclosed chamber pancreatic islet cells; and passing body fluid through one or more hollow fibres extending in said chamber, each said fibre having a porosity allowing substances of molecular weight less than 100,000 Daltons to diffuse and to thereby treat said body fluid.

10. A process as defined in claim 9, wherein, when said container is attached to an animal, said pancreatic islet cells are of the same species as the animal.

11. A process as defined in claim 9, wherein, when said container is attached to an animal, said pancreatic islet cells are of a different species than that of said animal.

12. Process as in claim 9, including the further step of implanting said container.

* * * * *